United States Patent [19]

Bünger et al.

[11] 4,372,875

[45] Feb. 8, 1983

[54] METHOD FOR OBTAINING AND REUSING OF OXIDATION CATALYST IN THE WITTEN DMT PROCESS

[75] Inventors: Heinrich Bünger, Siegburg; Rudolf Cordes; Gerhart Hoffmann, both of Niederkassel, all of Fed. Rep. of Germany

[73] Assignee: Dynamit Nobel Aktiengesellschaft, Troisdorf, Fed. Rep. of Germany

[21] Appl. No.: 326,280

[22] Filed: Dec. 1, 1981

Related U.S. Application Data

[63] Continuation of Ser. No. 156,605, Jun. 5, 1980, abandoned.

[30] Foreign Application Priority Data

Jun. 12, 1979 [DE]  Fed. Rep. of Germany ....... 2923681

[51] Int. Cl.$^3$ .................... B01J 31/40; C07C 69/82
[52] U.S. Cl. .................... 252/413; 252/414; 252/420; 560/77
[58] Field of Search ............... 252/412, 413, 414, 420; 560/77, 78; 423/49

[56] References Cited

U.S. PATENT DOCUMENTS

| | | | |
|---|---|---|---|
| 2,894,498 | 7/1959 | Katzschmann | 560/77 |
| 3,551,481 | 12/1970 | Hulsman | 560/78 |
| 3,914,287 | 10/1975 | Takeda et al. | 560/77 |
| 4,092,481 | 5/1978 | Bunger | 560/77 |
| 4,096,340 | 6/1978 | Fujii et al. | 560/77 |
| 4,126,755 | 11/1978 | Bunger et al. | 560/77 |

FOREIGN PATENT DOCUMENTS 47-35898  9/1972  Japan .................... 560/78

*Primary Examiner*—P. E. Konopka
*Attorney, Agent, or Firm*—Antonelli, Terry and Wands

[57] ABSTRACT

A process for effecting the recovery and use of a heavy metal oxidation catalyst from a high-boiling distillation residue obtained during the Witten process for the production of dimethyl terephthalate involves the extraction of the high-boiling distillation reside with water or dilute aqueous solution of low molecular weight aliphatic monocarboxylic acids or alcohols and recycling of the extract into the oxidation stage of the Witten process. In the extract the quantitative ratio of the sum of the amount of trimellitic acid and monomethyl ester of trimellitic acid to the amount of heavy metal catalyst is controlled to be at a value of no more than 1.8:1 and in the oxidation stage of the Witten process the catalyst concentration (c), expressed in p.p.m., is represented by the formula:

$$c = 44 \cdot (a/b) + d$$

wherein a represents the sum of trimellitic acid and monomethyl ester of trimellitic acid, b is the amount of heavy metal oxidation catalyst within the extract, and d is in a range of from 60 to 300 p.p.m.

15 Claims, No Drawings

METHOD FOR OBTAINING AND REUSING OF OXIDATION CATALYST IN THE WITTEN DMT PROCESS

This is a continuation of application Ser. No. 156,605, filed June 5, 1980, now abandoned.

The invention relates to an improved method for obtaining and reusing a heavy metal oxidation catalyst by the extraction of high-boiling distillation residues— these residues being produced during the oxidation of mixtures which contain p-xylene and/or methyl p-toluate in the liquid phase with oxygen or an oxygen-containing gas at an elevated pressure and elevated temperature in the presence of a dissolved heavy metal oxidation catalyst, subsequent esterification of the oxidation product with methanol at elevated pressure and elevated temperature, and separation of the esterification product by distillation into a crude dimethyl terephthalate (DMT) fraction, a fraction rich in methyl p-toluate, and a high-boiling distillation residue—with water or dilute aqueous solutions of low-molecular aliphatic monocarboxylic acids or alcohols and recycling of the extract into the oxidation stage, optionally after concentration.

Dimethyl terephthalate (DMT) is required as a raw material for the manufacture of polyester by reaction with ethylene glycol or tetramethylene glycol for fibers, filaments, films, or molded components. DMT is produced in numerous large-scale technical plants in accordance with the Witten-DMT process (as disclosed in the German Pat. No. 1,041,945 and U.S. Pat. No. 2,894,978).

In this method, a mixture of p-xylene (PX) and methyl p-toluate (PTE) is oxidized in the absence of solvents and halogen compounds in the liquid phase at elevated pressure and elevated temperature with oxygen or an oxygen-containing gas in the presence of a dissolved heavy metal oxidation catalyst, especially a mixture of cobalt and manganese (also note DAS [German Published Application] No. 2,010,137).

Thereafter the thus-obtained reaction mixture consisting predominantly of monomethyl terephthalate (MMT) and p-toluic acid (PTA) is esterified with methanol. The esterification product is separated by distillation into a PTE fraction, a DMT fraction, and a high-boiling, tarry residue. The PTE fraction is recycled into the oxidation stage. The high-boiling, tarry distillation residue contains, inter alia, all of the catalyst components, e.g. cobalt and manganese. The organic components of the residue are acids, substituted biphenyls, substituted triphenyls, esters of p-hydroxy-methyl-benzoic acid and other not identified components.

It is advantageous to recover the oxidation catalyst from the tarry distillation residue and reuse this catalyst for the oxidation of PX and PTE.

It is possible to combust the tarry distillation residue, thus converting a major part of the metal components of the heavy metal oxidation catalyst into oxides, and to obtain the oxides in the form of an ash. The ash can be obtained from the combustion air, for example with the aid of cyclones or with electrostatic filters.

In this mode of operation, however, cobalt losses are incurred by the formation of volatile cobalt compounds. Besides the ash cannot be reused directly as the oxidation catalyst. The ash must first be dissolved in mineral acids; then the heavy metals must be removed by precipitation. The thus-formed precipitates contain, in addition to the heavy metals usable as the oxidation catalysts, undesired impurities, e.g. iron and chromium stemming from a corrosion of the material of the apparatus, and additionally vanadium if the tarry distillation residues are combusted with the aid of heavy fuel oil.

It has furthermore been proposed to obtain the oxidation catalyst from the tarry distillation residue formed in the DMT production according to the Witten process by liquid-liquid extraction, and to recycle the catalyst-containing extract directly into the oxidation stage. The extractants proposed were: water, water with simultaneous introduction of air, mixtures of water and lower aliphatic alcohols, as well as mixtures of water and lower aliphatic fatty acids (as disclosed in DAS No. 2,531,106).

These extraction methods have the disadvantage that the catalytic selectively for oxidation of the thus-obtained heavy-metal catalyst containing extracts, designated hereinafter as "regenerated catalyst solutions," is lower than that of equally concentrated solutions of fresh oxidation catalyst, and that the catalytic selectively of the regenerated catalyst solutions is not constant but rather can assume very differing values in spite of a constant metal content.

The lower and inconstant catalytic selectivity has the effect that the DMT yield can be more than 4 molar percent lower than with the use of a fresh oxidation catalyst, and that the combustion losses are higher, especially due to the increased formation of carbon monoxide and carbon dioxide. Especially because of the inexplicable and unforeseeable inconstancy of the selectivity, the use of the regenerated catalyst solution has heretofore caused great difficulties in technical oxidation plants.

To increase and stabilize the selectivity of the regenerated catalyst DOS [German Unexamined Laid Open Application] No. 2,525,135 proposed either to treat the tarry distillation residue prior to liquid-liquid extraction with methanol at an elevated temperature under certain conditions, and only thereafter to extract the heavy metals, e.g. cobalt and manganese; or initially to extract the heavy metals from this tarry distillation residue and then to treat the extract with methanol at an elevated temperature under specific conditions (if necessary, after previous removal of a portion or of the entire amount of the extraction solvent). This mode of operation to activate the regenerated catalyst requires special apparatus to establish an intimate contact of the residue or extract with the methanol. Since this process involves the handling of considerable quantities of methanol at an elevated temperature, energy consumption is increased and losses of methanol are encountered.

Therefore, one object of the present invention resides in developing a process for the recovery of oxidation catalyst from the catalyst-containing distillation residue obtained in the manufacture of DMT according to the Witten process and for reusing the recovered catalyst for the oxidation of PX and/or PTE according to the Witten process without impairing the selectivity of the oxidation, without producing any larger amounts of carbon dioxide and carbon monoxide than are produced with a fresh catalyst and without treating an extract or a non-extracted residue with methanol.

It is necessary to utilize minimum amounts of catalyst in the oxidation of the DMT process to maintain the catalyst expenses at a low level and to avoid disturbances in the esterification required after the oxidation. Concentrations of oxidation catalyst which are too high lead to clogging in the esterification columns by deposits of catalyst metal. This clogging is avoided, and the costs of recovery and the losses unavoidable in any recovery are reduced, if minimum quantities of catalyst are used in the oxidation stage. The metered feeding of small amounts of regenerated catalyst, however, has not been possible, heretofore, without a reduction in the DMT yield, since the selectivity of the regenerated catalyst solutions, for reasons inexplicable thus far, is inconstant in spite of a constant metal content. Therefore, a further object of the present invention resides in developing a process making it possible to use the thus-recovered oxidation catalyst in the oxidation stage in quantities which are as small as possible, without impairing the selectivity of the oxidation.

Additional objects and advantages can be seen from the following description of the invention.

Our investigations have shown, surprisingly, that the catalyst-containing extract from the catalyst-containing distillation residue obtained according to the Witten process contains varying amounts of trimellitic acid (TMA) and the monomethyl ester of trimellitic acid (TMME); that these compounds affect the minimally permissible catalyst concentration in the oxidation product; and that consequently, with the use of such regenerated catalyst solutions, difficulties and losses in yield of more than 4 molar percent are encountered which do not occur in the absence of TMA and TMME.

These results are the more surprising, inasmuch as it is indicated in JA-AS 1239/78 of Jan. 17, 1978 that by the addition of TMA during the extraction of oxidation catalyst, the catalytic selectivity of the catalyst-containing extract is increased; for this reason, a considerable technical prejudice had to be overcome by the present invention.

It is furthermore surprising that the difficulties and losses in yield when using TMA-containing catalyst solutions are observed at the technically preferred oxidation conditions, for example in a continuous oxidation in reactor cascades under an excess pressure of 4–8 bar, but are not observed in the discontinuous oxidation under normal pressure, as customary in the laboratory for testing the catalyst.

All objects are attained, according to the invention, by recovering the oxidation catalyst by liquid-liquid extraction from the above-described, catalyst-containing distillation residue; by utilizing the optionally concentrated extract for the oxidation of PX and PTE according to the Witten process; by setting during this procedure specific critical catalyst concentrations in the oxidation product depending on the quantitative ratio between TMA and TMME, on the one hand, and the heavy metal oxidation catalyst, on the other hand, in the regenerated catalyst solution; and by adjusting this quantitative ratio to a suitable value.

The difficulties and losses in yield can be avoided according to the invention by adjusting in the extract the quantitative ratio a/b of trimellitic acid plus monomethyl ester of trimellitic acid to the heavy metal oxidation catalyst to a value of at most 1.8:1, and by setting, in the oxidation stage the catalyst concentration (c) expressed in p.p.m. to $c = 44 \cdot (a/b) + d$, with 60 p.p.m. $\leq d \leq 300$ p.p.m. and with the above-mentioned value of the ratio a/b.

The catalyst concentration in the oxidation stage, i.e. in the reaction mixture employed during the oxidation, is set so that it is no lower than the minimum concentration $c_{min}$ given by Formula (1):

$$c_{min} = 44 \cdot (a/b) + 60 \quad (1)$$

wherein $c_{min}$ indicates the minimum concentration of the heavy metal catalyst in the oxidation stage, in p.p.m.; whereas a is the sum total of the concentrations of TMA and TMME in the regenerated catalyst solution in gram/liter, and b is the concentration of the heavy metal catalyst in this solution, likewise in gram/liter. The quotient a/b, accordingly, indicates the quantitative ratio of TMA+TMME to the heavy metal oxidation catalyst in the solution.

To increase the operating safety, however, catalyst concentrations which are not below the minimum concentration hereinafter indicated by Formula (2) are to be preferred, and catalyst concentrations not below the minimum concentration set forth by Formula (3) are especially preferred.

$$c_{min} = 44 \cdot (a/b) + 80 \quad (2)$$

$$c_{min} = 44 \cdot (a/b) + 90 \quad (3)$$

If the catalyst concentrations in the oxidation stage are set to be too high, the esterification columns can be clogged up; furthermore, the expenses for recovery are higher and the catalyst losses are greater. These difficulties can be avoided according to the invention without disadvantages by setting catalyst concentrations in the oxidation stage which are no lower than the minimum concentrations given by Equations (1)–(3) and no higher than the maximum concentration $c_{max}$, indicated in p.p.m., given by Formula (4) below. Catalyst concentrations not above the highest concentration given by Formula (5) are to be preferred, and catalyst concentrations not above the highest concentration given by Formula (6) are especially preferred.

$$c_{max} = 44 \cdot (a/b) + 300 \quad (4)$$

$$c_{max} = 44 \cdot (a/b) + 200 \quad (5)$$

$$c_{max} = 44 \cdot (a/b) + 130 \quad (6)$$

The catalyst concentration necessary in the oxidation stage as well as in the oxidation reaction mixture or product according to this invention rises with an increasing TMA and TMME content in the regenerated catalyst solution, based on its content of the oxidation catalyst. For this reason, a high TMA and TMME content in the solution, based on the oxidation catalyst, is uneconomical. According to the invention, a quantitative ratio of at most 1.8 gram of TMA and TMME per gram of oxidation catalyst is employed; at most 1.0 gram of TMA and TMME per gram of oxidation catalyst is to be preferred; even more preferred is at most 0.8 gram of TMA and TMME per gram of oxidation catalyst.

The methods employed for setting these quantitative ratios of TMA and TMME to oxidation catalyst according to this invention are uncritical. These quantitative ratios can be set, for example by the further addition of soluble compounds of the heavy metal oxidation catalyst. It is also possible to mix a regenerated catalyst solution having a high TMA content with a catalyst solution containing a small amount of TMA, in a suitable ratio, resulting in a solution having the appropriate concentrations according to the invention.

Furthermore, TMA and TMME can be removed from the aqueous regenerated catalyst solutions with weakly alkaline anion-exchange resins. Especially well suitable are macroporous weakly alkaline anion-exchange resins in the acetate or formate form. Thereby TMA, TMME, and other di- and tri-carboxylic acids contained in the catalyst solution are exchanged against acetic acid or formic acid and selectively removed from the catalyst solution. Exemplary of suitable anion exchange resins are "Lewatit MP 62", supplied by Bayer AG, Leverkusen, or "Permutit EM-13", supplied by Permutit Gesellschaft mbH, Berlin.

It is also possible to remove TMA and trimellitic acid ester prior to extraction by treatment with anion-exchange resins or by distillation from the residue to be extracted. Furthermore, it is possible to reduce the undesired conversion of water-insoluble higher trimellitic acid esters into watersoluble TMA and watersoluble TMME by gentle conditions, e.g. by a low thermal load on the residue during the separation of DMT and other useful products, or by low temperatures and/or short residence times in the extractor and/or during an evaporation of the catalyst solution which may follow extraction. The concentration of trimellitic acid and monomethyl ester of trimellitic acid in the regenerated catalyst solutions may be reduced to a range of from 0.001 to 5 grams/liter.

Dilute aqueous acetic acid solutions are suitably utilized for the extraction of the oxidation catalyst from the distillation residues, especially the oxidation wastewaters which contain acetic acid and formic acid, obtained in the oxidation of PX and PTE according to the Witten process. The extraction can be conducted according to various extraction methods, for example in a discontinuous or continuous operation, in a single-stage or multistage process, in mixer-settlers, or in columns. The continuous extraction in mixer-settlers is preferred.

The invention is applicable to the oxidation catalysts known for the oxidation of PX and PTE, preferably to catalysts of the cobalt-manganese type containing cobalt and manganese in weight ratios of 40:1 to 2:1, especially advantageously of 20:1 to 5:1. The regenerated catalyst solution is introduced in the oxidation stage continuously, but also discontinuously.

The following examples will serve to further explain the invention.

EXAMPLE 1

(Comparative Example)

A regenerated catalyst solution was obtained from a distillation residue produced in an industrial plant for DMT manufacture according to the Witten process. In this plant, PX and PTE were continuously oxidized together in the liquid phase under an excess pressure of 5–7 bar and at a reaction temperature of 150°–170° C.; the oxidation catalyst was a freshly prepared solution of cobalt acetate and manganese acetate in 2% aqueous acetic acid. This solution was fed continuously so that a stationary concentration of 90 p.p.m. of cobalt and 9 p.p.m. of manganese was obtained in the oxidation product. The oxidation product contained, in addition to the aforementioned catalyst and the thus-formed carboxylic acids, unreacted starting compound and various intermediates and by-products. This oxidation product was continuously esterified with methanol at temperatures of about 250° C. and under pressure of between 20 and 30 bar. The esterification product was continuously separated by fractionation at 200 mbar and 220°–260° C. The residue boiling higher than DMT contained acids, substituted biphenyls, substituted triphenyls, esters of p-hydroxy-methyl-benzoic acid and not identified components. This residue was subjected to a thermal after-treatment for about 15 hours at 100 mbar and 250°–270° C., thus obtaining additional DMT by thermolytic reactions and distillation of the reaction products from the high-boiling components. Equal amounts of distillation residue and extractant were fed continuously to an agitator-equipped mixing vessel. The temperature of the residue was 150° C., the temperature of the extractant was 50° C.; a temperature of 95° C. was set in the mixing vessel. The extractant employed was water of reaction obtained as vapor condensate during the above-described industrial oxidation of PX and PTE and containing on the average 2.5% by weight acetic acid, 1.5% by weight formic acid, and 0.8% by weight formaldehyde. Through a bottom valve of the mixing vessel, an emulsion was continuously discharged and separated in a settling tank into an aqueous phase and an organic phase. The aqueous phase was concentrated under normal pressure; any thus-precipitated, insoluble components were separated. The sum total of the concentrations of TMA and TMME in the concentrated solution was 59.3 g./l. as determined by polarographic analysis. The cobalt and manganese concentrations were determined by titrimetry and amounted to 35 g./l. of cobalt and 3.5 g./l. of manganese. The solution accordingly contained 1.54 g. of TMA+TMME, based on one gram of oxidation catalyst.

This regenerated catalyst solution was used, in place of the above-described, freshly prepared catalyst solution, continuously in the industrial plant for DMT manufacture; the other operating parameters were not altered. After four days the carbon dioxide concentration in the oxidation waste gas had risen to 3–5% by volume as compared to 1.8–2.2 before changing the catalyst. The carbon monoxide concentration in the oxidation waste gas simultaneously rose from 0.6–0.8% by volume to 0.9–1.0% by volume.

The DMT yield, based on xylene, was lower by 4.5 molar percent with the use of the regenerated catalyst than with the use of the freshly prepared catalyst.

EXAMPLE 2

(Comparative Example)

The regenerated catalyst solution described in Example 1 was tested in a continuously operated experimental reactor of stainless steel. The indicator for changes in selectivity was represented by the concentrations of carbon monoxide and carbon dioxide in the oxidation waste gas. If the oxidation rate is constant, these concentrations are directly suitable as a measure of selectivity, because the yield-reducing secondary reactions lead predominantly to carbon monoxide and carbon dioxide, and because the formation of residue is in a positive correlation to the formation of carbon monoxide and carbon dioxide. A constant oxidation rate was attained by feeding air to the reactor at a constant rate, and by choosing the oxidation conditions so that the oxygen was completely absorbed in all cases.

The experimental reactor had an internal diameter of 40 cm. and a useful volume of 1.8 m$^3$; the reactor was equipped with an air feed pipe, a twin jacket for heating or cooling, a water trap, measuring the control devices for feeding PX and PTE, draining devices, as well as metering pumps for feeding catalyst solution. The catalyst solution described in Example 1, freshly prepared from cobalt acetate and manganese acetate was continuously pumped into the head of this reactor, along with 80 kg. of PX and 93 KG. of PTE per hour. PX and PTE were taken from operating tanks of the technical DMT plant described in Example 1. Such an amount of catalyst solution was utilized that a stationary concentration of 90 p.p.m. of cobalt and 9 p.p.m. of manganese was obtained in the oxidation product. This concentration was tested by the regular withdrawal and analysis of samples. By means of a level control device, liquid was continuously discharged from the experimental reactor through a bottom valve so that the liquid content of the reactor was maintained at 1.7 m$^3$. The temperature in the sump of the reactor was kept at 159° C. by a temperature control device. At the bottom of the reactor, 60 Nm$^3$ of air was introduced per hour. Gas was continuously exhausted via an expansion valve from the head of the reactor with the aid of a pressure control device, so that an excess pressure of 6 bar was obtained in the gas space of the reactor. These reaction conditions correspond to those in the first reactor of a three-stage large scale industrial reactor cascade.

The condensible components discharged with the oxidation waste gas were condensed in a cooler; thereafter the concentrations of oxygen, carbon monoxide and carbon dioxide in the oxidation waste gas were measured continuously. After a one-day operation the oxidation waste gas contained 0.6% by volume of carbon monoxide, 1.8% by volume of carbon dioxide, and less than 0.1% by volume of oxygen. This waste gas composition did not vary within five days of continuous operation. After these five days, the regenerated catalyst solution described in Example 1 was pumped continuously into the reactor head in place of the fresh catalyst solution. The cobalt and manganese concentrations in the oxidation product were maintained, as before, at 90 p.p.m. of cobalt and 9 p.p.m. of manganese. After converting to regenerated catalyst solution, the concentrations of carbon monoxide and carbon dioxide in the waste gas gradually increased. Four days after conversion, these concentrations were 0.8% by volume of carbon monoxide and 3.5% by volume of carbon dioxide and the yield of DMT based on xylene, was lowered by about 4 molar percent.

EXAMPLE 3

TMA and TMME were removed from the regenerated catalyst solution described in Example 1 by absorption on a weakly alkaline anion-exchange resin. For this purpose. a resin having the trade name "Lewatit MP 62" by Bayer AG in Leverkusen was activated in a column with 4% strength sodium hydroxide solution. The column was then flushed with the water of reaction obtained from the industrial oxidation of PX and PTE and containing acetic acid and formic acid, described in Example 1, and thereby the resin was loaded with acetate and formate ions. Subsequently, the regenerated catalyst solution was introduced at the top of the column at 60° C. and withdrawn at the bottom. The eluate contained the catalyst solution and traces of the flushing water. The eluate was concentrated until the cobalt concentration was again 35.0 g./l.; in addition, the thus-concentrated solution contained 3.5 g./l. of manganese and less than 0.1 g./l. of TMA and TMME.

This catalyst-containing solution was tested as described in Example 2. After conversion from the fresh catalyst solution to this regenerated catalyst solution freed of TMA and TMME, no change in the waste gas composition occurred. After five days of continuous operation with the regenerated catalyst freed of TMA and TMME, the waste gas contained, as before, 0.6% by volume of carbon monoxide, 1.8% by volume of carbon dioxide, and less than 0.1% by volume of oxygen.

EXAMPLE 4

The TMA- and TMME-containing regenerated catalyst solution described in Example 1 was mixed in various proportions with the regenerated catalyst solution described in Example 3, from which TMA and TMME had been removed. Various regenerated catalyst solutions resulted, all of which contained 35 g./l. of cobalt and 3.5 g./l. of manganese, but differing concentrations of TMA and TMME. These solutions were tested analogously to Example 2 in a continuously operated experimental reactor, but initially, with fresh catalyst, concentrations were set of 300 p.p.m. of cobalt and 30 p.p.m. of manganese in the oxidation reaction product. Then conversion was effected with a regenerated catalyst and the oxidation was continued at a catalyst concentration of 300 p.p.m. of cobalt and 30 p.p.m. of manganese. Under these conditions the composition of the oxidation waste gas remained unchanged; the waste gas contained, as before, 0.6% by volume of carbon monoxide, 1.8% by volume of carbon dioxide, and less than 0.1% by volume of oxygen. At this point in time, the metered feeding of the catalyst was reduced gradually in small steps; the catalyst concentration in the oxidation product was determined regularly, and the waste gas composition was measured continuously. The oxygen concentration in the oxidation waste gas was in all cases below 0.1% by volume; the carbon dioxide concentration started to rise when the catalyst concentration was allowed to fall short of certain critical values. The minimum permissible catalyst concentrations were determined to be those at which the carbon dioxide concentration in the waste gas was 2.1% by volume. These minimum permissible catalyst concentrations were dependent on the quantitative ratio between TMA+TMME on the one hand and heavy metal oxidation catalyst on the other hand in the regenerated catalyst solution. Table 1 shows this dependency.

TABLE 1

| Example No. | Quantitative Ratio $\frac{a}{b}$ in Catalyst Solution g. (TMA + TMME) g. Catalyst | Catalyst Concentration in Oxidation Product with 2.1% by Volume of CO$_2$ in the Waste Gas [p.p.m. (Co + Mn)] |
|---|---|---|
| 4.1 | 0 | 73 |
| 4.2 | 0.40:1 | 82 |
| 4.3 | 0.88:1 | 100 |
| 4.4 | 1.02:1 | 110 |
| 4.5 | 1.20:1 | 116 |
| 4.6 | 1.54:1 | 132 |

The carbon dioxide concentration in the waste gas is an indicator for changes in selectivity of the oxidation. This concentration is directly suitable as a measure of selectivity, and at a carbon dioxide concentration of more than 2.1 by volume the selectivity of the oxidation is too low.

What is claimed is:

1. A process for obtaining and reusing a heavy metal oxidation catalyst in the production of dimethyl terephthalate by the extraction of high-boiling distillation residues, said residues being produced during the oxidation of mixtures which contain p-xylene and/or methyl p-toluate in the liquid phase with oxygen or an oxygen-containing gas at an elevated pressure and elevated temperature in the presence of the dissolved heavy metal oxidation catalyst, subsequent esterification of the oxidation product with methanol at elevated pressure and elevated temperature, and separation of the esterification product by distillation into a crude dimethyl terephthalate fraction, a fraction rich in methyl p-toluate, and a high-boiling distillation residue, with water or dilute aqueous solutions of low-molecular weight aliphatic monocarboxylic acids or alcohols and recycling of the extract which contains the heavy metal oxidation catalyst trimellitic acid and the monomethyl ester of trimellitic acid into the oxidation stage, optionally after concentration, characterized in that in the extract the quantitative ratio a/b of the concentration (a) in gram/liter of trimellitic acid plus the monomethyl ester of trimellitic acid to the concentration (b) in gram/liter of heavy metal oxidation catalyst is reduced to a value of no more than 1.8:1 and that in the oxidation stage the catalyst concentration c, expressed in p.p.m., is represented by the formula: $c = 44 \cdot (a/b) + d$, with 60 p.p.m. $\leq d \leq$ 300 p.p.m., and with the ratio of a/b having said value prior to the recycling of the extract.

2. A process according to claim 1, characterized in that the concentration of trimellitic acid plus the monomethyl ester of trimellitic acid in the extract is reduced by ion exchange with the acetate and/or formate form of weakly alkaline ion-exchange resins.

3. A process according to claim 1, wherein the heavy metal oxidation catalyst in the extract comprises a mixture of cobalt and manganese in a weight ratio of 40:1 to 2:1.

4. A process according to claim 3, wherein the oxidation of the mixture of p-xylene and methyl p-toluate is conducted with air at a temperature of from 150°–170° C. and at pressures from 5–7 bar with a total catalyst concentration of from 60 to approximately 379 p.p.m.

5. A process according to claim 2, wherein the concentration of trimellitic acid and monomethyl ester of trimellitic acid in the regenerated catalyst solutions is reduced to a range of from 0.001 to 5 grams/liter.

6. A process according to claim 1, wherein the high-boiling distillation residue is extracted with an aqueous acetic acid solution to form said extract containing the heavy metal catalyst and trimellitic acid and the monomethyl ester of trimellitic acid.

7. A process according to claim 1, wherein the minimum concentration of the catalyst in the oxidation stage is represented by the formula:

$$c = 44 \cdot (a/b) + 60$$

8. A process according to claim 1, wherein the minimum concentration of the catalyst in the oxidation stage is represented by the formula:

$$c = 44 \cdot (a/b) + 80$$

9. A process according to claim 1, wherein the minimum concentration of the catalyst in the oxidation stage is represented by the formula:

$$c = 44 \cdot (a/b) + 90$$

10. A process according to claim 7, wherein the maximum concentration of the catalyst in the oxidation stage is represented by the formula:

$$c = 44 \cdot (a/b) + 300$$

11. A process according to claim 8, wherein the maximum concentration of the catalyst in the oxidation stgage is represented by the formula:

$$c = 44 \cdot (a/b) + 200$$

12. A process according to claim 9, wherein the maximum concentration of the catalyst in the oxidation stage is represented by the formula:

$$c = 44 \cdot (a/b) + 130$$

13. A process according to claim 2, wherein the ratio of a/b is no more than 1:1.

14. A process according to claim 1, wherein the ratio of a/b is no more than 0.8:1.

15. A process according to claim 1, wherein the ratio of a/b is in the range of from 0.40:1 to 1.54:1.

* * * * *